(12) United States Patent
Dubois et al.

(10) Patent No.: US 7,463,366 B2
(45) Date of Patent: Dec. 9, 2008

(54) DIGITAL HOLOGRAPHIC MICROSCOPE

(75) Inventors: Franck Dubois, Brussels (BE); Catherine Yourassowsky, Brussels (BE)

(73) Assignee: Universite Libre De Bruxelles, Bruxelles (BE)

( * ) Notice: Subject to any disclaimer, the term of this patent is extended or adjusted under 35 U.S.C. 154(b) by 190 days.

(21) Appl. No.: 11/284,768

(22) Filed: Nov. 22, 2005

(65) Prior Publication Data

US 2006/0132799 A1 Jun. 22, 2006

Related U.S. Application Data

(63) Continuation-in-part of application No. 10/742,054, filed on Dec. 18, 2003, now Pat. No. 7,009,700, which is a continuation of application No. PCT/BE02/00111, filed on Jul. 1, 2002.

(51) Int. Cl.
*G01B 9/02* (2006.01)
(52) U.S. Cl. ...................................................... 356/520
(58) Field of Classification Search ................ 356/457, 356/458, 497, 479, 519, 520
See application file for complete search history.

(56) References Cited

U.S. PATENT DOCUMENTS

| | | | |
|---|---|---|---|
| 2,770,166 A | 11/1956 | Gabor | |
| 3,867,009 A | 2/1975 | Pawluczyk | |
| 4,827,125 A | 5/1989 | Goldstein | |
| 5,365,354 A | 11/1994 | Jansson et al. | |
| 6,020,963 A * | 2/2000 | DiMarzio | 356/491 |
| 6,038,041 A | 3/2000 | Poon et al. | |
| 6,496,267 B1 | 12/2002 | Takaoka | |
| 6,525,821 B1 * | 2/2003 | Thomas et al. | 356/457 |

FOREIGN PATENT DOCUMENTS

WO    WO 98/13715    4/1998

(Continued)

OTHER PUBLICATIONS

Liu et al, "Off-axis holographic technique for partical image velocimetry using a Fourier-transform lens" Feb. 1, 1995, vol. 20 No. 3, Optics Letters.*

(Continued)

*Primary Examiner*—Tarifur R Chowdhury
*Assistant Examiner*—Jonathon D Cook
(74) *Attorney, Agent, or Firm*—Knobbe Martens Olson & Bear LLP (57) ABSTRACT

A method and device for obtaining a sample with three-dimensional microscopy, in particular a thick biological sample and the fluorescence field emitted by the sample. One embodiment includes obtaining interferometric signals of a specimen, obtaining fluorescence signals emanating from the specimen, recording these signals, and processing these signals so as to reconstruct three-dimensional images of the specimen and of the field of fluorescence emitted by the specimen at a given time. Another embodiment includes a digital holography microscope, a fluorescence excitation source illuminating a specimen, where the microscope and the fluorescence excitation source cooperate to obtain interferometric signals of the specimen and obtain fluorescence signals emanating from the specimen, means for recording the interferometric signals and fluorescence signals, and means for processing the interferometric signals and the fluorescence signals so as to reconstruct three-dimensional images of the specimen and of the field of fluorescence emitted by the specimen at a given time.

16 Claims, 5 Drawing Sheets

FOREIGN PATENT DOCUMENTS

WO     WO 00/20929     4/2000

OTHER PUBLICATIONS

Gittens et al, "Interference model for back-focal-plane displacement detection in optical tweezers" Jan. 1, 1998, vol. 23 No. 1, Optics Letters.*

Cuche et al., "Digital holograph for quantitative phase-contrast imaging," Optics Letters, vol. 24, No. 5, pp. 291-293, Mar. 1, 1999.

Dubois et al., "Improved three-dimensional imaging with a digital holography microscope with a source of partial spatial coherence," Applied Optics, vol. 38, No. 34, pp. 7085-7094, Dec. 1999.

Kirkpatrick et al., "Optimization by Simulated Annealing," Science, vol. 220, No. 4598, pp. 671-679, May 13, 1983.

Schilling et al., "Three-dimensional holographic fluorescence microscopy," Optics Letters, vol. 22, No. 19, pp. 1506-1508, Oct. 1, 1997.

Skarman et al., "Simultaneous 3D-PIV and temperature measurements using a new CCD holographic interferometer," Flow Measurement Instrumentation, vol. 7, No. 1, pp. 1-12, 1996.

Takaki et al., "Hybrid holographic microscopy: visualization of three-dimensional object information by use of viewing angles," Applied Optics, vol. 39, No. 29, pp. 5302-5308, Oct. 10, 2000.

Takeda et al., "Fourier-transform method of fringe-pattern analysis for computer-based topography and interferometry," J. Opt. Soc. Am., vol. 72, No. 1, pp. 156-160, Jan. 1982.

Zhang et al., "Three-dimensional microscopy with phase-shifting digital holography," Optics Letters, vol. 23, No. 15, pp. 1221-1223, Aug. 1, 1998.

* cited by examiner

DIGITAL HOLOGRAPHIC MICROSCOPE

RELATED APPLICATIONS

This application is a continuation in part of U.S. application Ser. No. 10/742,054 filed on Dec. 18, 2003, now U.S. Pat. No. 7,009,700, which is hereby incorporated by reference. U.S. application Ser. No. 10/742,054 is a continuation application under 35 U.S.C. § 120 of WO 03/002972, filed as PCT/BE02/00111 on Jul. 1, 2002.

FIELD OF THE INVENTION

The present invention relates to a method and to an instrument for obtaining three-dimensional images of a specimen or sample by microscopy and for obtaining, in three dimensions, the field of fluorescence emitted by this specimen, said specimen being either fluorescent or prelabeled using one or more fluorochromes.

The present invention also relates to a particular microscope for obtaining three-dimensional images of a specimen.

One of the applications of said method and of said instrument relates more particularly to obtaining three-dimensional images of the fluorescence emitted by biological specimens, that may be thick, for the purpose of observing their dynamic behavior and their change over time.

PRIOR ART

Conventional fluorescence microscopy has provided substantial progress in the field of biology. In particular, the technique of immunofluorescence has made it possible to carry out specific labeling of molecules and their location in tissues. Moreover, the discovery of GFPs (green fluorescent proteins) has revolutionized the study of locating proteins in living cells and of determining the dynamics and interactions of said proteins.

However, one of the problems encountered in conventional fluorescence microscopy is that of the fluorescence emitted by elements lying outside the plane of sharpness. This parasitic light prevents good acquisition of the image by adding substantial background noise. The images become very difficult to interpret when thick biological specimens, such as embryons, are observed.

Confocal microscopy allows this problem to be overcome by exciting the fluorescence of the specimen over a very small area that scans the specimen and by blocking the fluorescence emitted outside the illuminated area by means of a small aperture.

However, confocal microscopy also has its own drawbacks.

One drawback of confocal microscopy is that this technique requires complete scanning of the specimen by an optomechanical device. This operation requires a relatively long time (typically of the order of a few seconds) to analyze a volume before the image is available to be displayed.

Furthermore, the exciting source used in confocal microscopy is generally an argon or argon-krypton laser that may damage biological specimens.

Another drawback is that the exciting sources do not allow the entire wavelength range needed for observation in fluorescence to be easily covered.

Finally, confocal microscopy is an extremely sophisticated technique that requires great precision during manipulation and is also expensive.

SUMMARY

Certain embodiments provide a method and an instrument for obtaining, by microscopy, three-dimensional images of a specimen, in particular a thick biological specimen, and for measuring, in three dimensions, the fluorescence emitted thereby, said method and said instrument not presenting the drawbacks of the conventional microscopy techniques, including those of confocal microscopy.

In particular, certain embodiments provide a method and an instrument for obtaining three-dimensional images of the specimen and of the fluorescence field of this specimen, that is to say for obtaining information about the distribution of the fluorescence over the entire volume of the specimen, and optionally to monitor their change over time, and to do so with a minimum time delay between each image acquisition.

Certain embodiments provide a method and a device that do not require excessive complex manipulation and which cost is thus competitive, especially compared with confocal microscopy.

Certain embodiments provide a microscope for obtaining easily high quality three-dimensional images of a specimen, and namely with minimal optical adjustments.

Certain embodiments relate to a method and to an instrument for obtaining three-dimensional images of a specimen, preferably a thick biological specimen, and to obtain, in three dimensions, the field of fluorescence emitted by said specimen, by coupling interferometric signals obtained by digital holography with fluorescence signals.

The term "thick specimen" is understood to mean a specimen whose dimensions are such that it is impossible to have a sharp image simultaneously over the entire depth of the specimen using a conventional optical microscopy method.

In one embodiment, there is a method for obtaining, by microscopy, three-dimensional images of a specimen, in particular a thick biological specimen, and of the field of fluorescence emitted by this specimen, characterized in that it comprises:

a measurement and recording step during which, on the one hand, interferometric signals obtained by digital holography and, on the other hand, fluorescence signals emanating from the specimen are measured and recorded sequentially and independently; and a processing step during which said interferometric signals obtained by digital holography and said fluorescence signals thus recorded are combined so as to reconstruct sharp three-dimensional images of the specimen itself and of the field of fluorescence emitted by said specimen at a given instant.

Preferably, said measurement and recording step and said processing step are repeated over the course of time so as to monitor the change in the three-dimensional images of the specimen and of the fluorescence field of said specimen.

Advantageously, the combining of the interferometric signals obtained by digital holography with the fluorescence signals, in order to reconstruct the sharp three-dimensional images of the specimen itself under study and of the fluorescence field of said specimen, is performed by numerical analysis.

In another embodiment, there is an instrument for implementing the method described above and which comprises a microscope operating in digital holography, combined with a source for exciting the fluorescence.

Preferably, the fluorescence excitation source operates in reflection mode or transmission mode.

Advantageously, the microscope operating in digital holography comprises a partially coherent, or optionally coherent, light source operating in transmission and capable of generating a source light beam.

Advantageously, the partially coherent light source is a partially spatially coherent light source.

According to a first preferred embodiment, the partially spatially coherent light source of said microscope comprises the following elements: a source emitting light of small spectral width, a first lens, a first aperture, a second lens, a second aperture and a third lens, the relative arrangement of these various elements being such that, when the source is operating, the light emitted by the light-emitting source encounters, in succession, the first lens, the first aperture, the second lens, the second aperture and the third lens, and the light at the exit of the third lens is collimated light.

According to another preferred embodiment, the partially spatially coherent light source of said microscope comprises the following elements: a source emitting light of small spectral width, an optical fiber, a first lens, a second lens, a third lens and an adjustable aperture, the relative arrangement of these various elements being such that, when the source is operating, the light emitted by the light-emitting source passes firstly through the optical fiber so as to have a homogeneous light field and then encounters the first lens, then the second lens and the third lens in order to obtain collimated light at the aperture.

According to another preferred embodiment, the partially spatially coherent light source of said microscope comprises the following elements: a laser source, a first lens, a rotating diffuser such as frosted glass, a second lens and an aperture, the relative arrangement of these various elements being such that, when the source is operating, the laser beam emitted by the laser source firstly encounters the first lens, then the rotating diffuser, which is placed behind the focal point of said first lens, then the second lens, placed at its focal length with respect to the plane of the rotating diffuser, and then said aperture.

According to another preferred embodiment, the partially spatially coherent light source of said microscope comprises the following elements: a laser source, a first lens, a rotating diffuser, such as a ground glass plate, and a second lens, the relative arrangement of these various elements being such that, when the source is operating, the laser beam emitted by the laser source firstly passes through the first lens, then the diffuser and then the second lens, the laser beam at the exit of the first lens being focused at a focal point located upstream of the diffuser at an adjustable distance from the diffuser. Such a source is used in the holographic microscope of the present invention without other lenses in said microscope, and more precisely without focusing elements (focuser) in the interferometer.

Preferably, the microscope operating in digital holography furthermore comprises:
  a movable first subassembly that comprises a beam splitter and a mirror, in order to form two parallel beams—an object beam and a reference beam—from the source light beam;
  a director device, corresponding to an element, preferably mirrors, for directing the source light beam onto the first subassembly at the beam splitter;
  a fixed or movable second subassembly, that also includes a beam splitter and a mirror, in order to combine said object beam and said reference beam into a recombined light beam;
  an object cell that includes a specimen to be studied, placed in the optical path of the object beam between the first subassembly and the second subassembly;
  a first microscope objective, in the optical path of the object beam between the first subassembly and the second subassembly, downstream of the object cell;
  an optical path compensation element (compensator) placed in the optical path of the reference beam between the first subassembly and the second subassembly;
  a second microscope objective placed in the optical path of the reference beam between the first subassembly and the second subassembly downstream of said optical path compensation element (compensator);
  a first focusing element (first focuser) capable of focusing the object beam onto the object cell; and
  a second focusing element (second focuser) capable of focusing the reference beam onto said optical path compensation element (compensator).

Preferably, said optical path compensation element or compensator comprises a reference cell similar to the object cell but not including the specimen to be studied.

Alternatively, said optical path compensation element (compensator) comprises a transparent material of suitable thickness and suitable composition.

Also possibly provided are a recording element (recorder) and a processing element (processor) preferably such as a CCD camera coupled to computer processing and an image analysis element (image analyzer), in order to record and process said interferometric signals and said fluorescence signals, and also an additional focusing element (additional focuser) in order to focus said recombined light beam onto said recording element (recorder).

Another embodiment relates directly to the microscope that can be used in the method and operates in digital holography, said microscope comprising:
  a partially coherent light source capable of generating a source light beam;
  a movable first subassembly that comprises a beam splitter and a mirror, in order to form two parallel beams—an object beam and a reference beam—from the source light beam;
  a director device, preferably mirrors, able to direct the source light beam onto the first subassembly at the beam splitter;
  a fixed or movable second subassembly, that also includes a beam splitter and a mirror, in order to combine said object beam and said reference beam into a recombined light beam;
  an object cell that includes a specimen to be studied, placed in the optical path of the object beam between the first subassembly and the second subassembly;
  a first microscope objective, in the optical path of the object beam between the first subassembly and the second subassembly, downstream of the object cell;
  an optical path compensation element (compensator) placed in the optical path of the reference beam between the first subassembly and the second subassembly;
  a second microscope objective placed in the optical path of the reference beam between the first subassembly and the second subassembly downstream of said optical path compensation element (compensator);
  a first focusing element (first focuser) capable of focusing the object beam onto the object cell; and
  second focusing means capable of focusing the reference beam onto said optical path compensation means.

More generally, another embodiment namely concerns a digital holographic microscope for obtaining three-dimensional images of a specimen to be studied comprising a light source, an interferometer, recording means defined by a sensitive plane and processing means, said microscope being conceived in such a manner that in operating conditions said light source provides a light beam, said interferometer separates said coherent light beam into a reference light beam and an object light beam, said object beam illuminates a specimen preliminary placed therein, said object and reference beams are recombined to produce interference patterns in the sensitive plane of the said recording means, the recording means records said interference patterns and said processing means processes said recorded interference patterns and reconstructs three-dimensional images of the specimen, wherein the interferometer comprises:
- a movable first subassembly that comprises a beam splitter and a mirror, for forming two parallel beams, an object beam and a reference beam, from the source light beam;
- a fixed or movable second subassembly comprising a beam splitter and a mirror so as to combine said object beam and said reference beam into a recombined light beam;
- an object cell, for receiving the specimen to be studied, said object cell being placed in the optical path of the object beam between the first subassembly and the second subassembly;
- a first microscope objective located in the optical path of the object beam between the first subassembly and the second subassembly, downstream of the object cell;
- compensation means for optimizing the equalization of the optical path lengths between the object beam and the reference beam, said compensation means being located in the optical path of the reference beam, between the first subassembly and the second subassembly;
- a second microscope objective located in the optical path of the reference beam between the first subassembly and the second subassembly, downstream said compensation means;

wherein the microscope further comprises focusing means defined by a back focal plane, said focusing means being placed between the interferometer and the recording means in such a way that the back focal plane of said focusing means is in the sensitive plane of the recording means.

More precisely, the position of the focusing means relatively to the interferometer and the recording means is such as to obtain in operating conditions an invariant positioning of the object beam and the reference beam on the sensitive plane of the recording means.

It means that in operating conditions the position of the reference beam and the position of the object beam on the sensitive plane of the recording means are invariant when the first subassembly and/or the second subassembly of the interferometer are moved.

The three-dimensional images thus obtained with the present microscope are of particularly high quality.

Moreover, the microscope require minimal optical adjustments when changing the specimen to be studied.

The microscope presents different technical advantages and features.

Advantageously, the microscope permits the obtention of three-dimensional images of the entire volume of a specimen without scanning.

The digital holographic microscope thus allows to obtain simultaneously in one step all the digital holographic information from the entire volume of the specimen. Said microscope also allows to process all said digital holographic information so as to reconstruct three dimensional-images of the entire volume of the specimen at a given time.

When the measurement, the recording and the processing are repeated over time, the microscope also allows to monitor possible changes in the three-dimensional images of the specimen.

However, it is still possible, with the microscope, to selectively obtain three-dimensional images of only a portion of the volume of a specimen.

The light source for illuminating the specimen, i.e., the source generating the light beam for illuminating the sample, may be partially spatially coherent or spatially coherent.

According to a certain embodiment of the present microscope, the first subassembly and the second subassembly are movable in rotation.

Preferably, the movements in rotation of the second subassembly are such as to allow in operating conditions the implementation of the Fourier transform method by the processing element (processor) for processing the interference patterns.

This Fourier transform method is a technique for processing interference patterns which is well known by the man skilled in the art.

According to another embodiment, the interferometer further comprises a first focusing element (first focuser) capable of focusing the object beam onto the object cell, and a second focusing element (second focuser) capable of focusing the reference beam onto said compensation element (compensator), the first subassembly being movable in rotation, the second subassembly being fixed in rotation and the mirror of the second subassembly being movable in translation.

Preferably, in this embodiment, the movements in translation of the mirror of the second subassembly are such as to allow in operating conditions the implementation of the phase-stepping method by the processing element (processor) for processing the interference patterns.

This phase-stepping method is a technique for processing interference patterns which is well known by the man skilled in the art.

Preferably, for this purpose, the mirror of the second subassembly is mounted on a piezo-electric motor.

Advantageously, in said embodiment, the microscope further comprises a director device able to direct the source light beam onto the first subassembly at the beam splitter.

Preferably, the director device or directing element comprises mirrors.

Concerning the partially spatially light source of the microscope, according to a first preferred embodiment, said partially spatially coherent light source comprises the following elements: a source emitting light of small spectral width, a first lens, a first aperture, a second lens, a second aperture and a third lens, the relative arrangement of these various elements being such that, when the source is operating, the light emitted by the light-emitting source encounters, in succession, the first lens, the first aperture, the second lens, the second aperture and the third lens, and the light at the exit of the third lens is collimated light.

According to another preferred embodiment, the partially spatially coherent light source comprises the following elements: a source emitting light of small spectral width, an optical fiber, a first lens, a second lens, a third lens and an adjustable aperture, the relative arrangement of these various elements being such that, when the source is operating, the light emitted by the light-emitting source passes firstly through the optical fiber so as to have a homogeneous light field and then encounters the first lens, then the second lens and the third lens in order to obtain collimated light at the aperture.

According to another preferred embodiment, the partially spatially coherent light source of said microscope comprises the following elements: a laser source, a first lens, a rotating diffuser, such as a frosted glas, a second lens and an aperture, the relative arrangement of these various elements being such that, when the source is operating, the light beam emitted by the laser source firstly passes through the first lens, then the rotating diffuser, which is placed behind the focal point of said first lens, then the second lens, placed at its focal length with respect to the plane of the rotating diffuser, and then said aperture.

According to another preferred embodiment, the partially spatially coherent light source comprises the following elements: a laser source, a first lens, a rotating diffuser, such as a ground glass plate, and a second lens, the relative arrangement of these various elements being such that, when the source is operating, the laser beam emitted by the laser source firstly passes through the first lens, then the diffuser and then the second lens, the laser beam at the exit of the first lens being focused at a focal point located upstream of the diffuser at an adjustable distance from the diffuser. Such a source is used in the holographic microscope without other lenses in said microscope, and more precisely without focusing elements (focusers) in the interferometer.

The optical path compensation element, also referenced herein as "compensation element" or "compensator", may comprise a reference cell similar to the object cell but not including the specimen to be studied, or a material of suitable thickness and suitable composition. Preferably, this material is a transparent material of suitable thickness and composition.

It should be noted that in the present description the terms "digital holographic information" and "interference pattern" are equivalent. As known by the man skilled in the art, an "interference pattern" comprises interference fringes.

DETAILED DESCRIPTION OF CERTAIN EMBODIMENTS

Light Sources Used for the Digital Holography

Different types of sources can be used for illuminating the sample to be studied.

Figure 1:
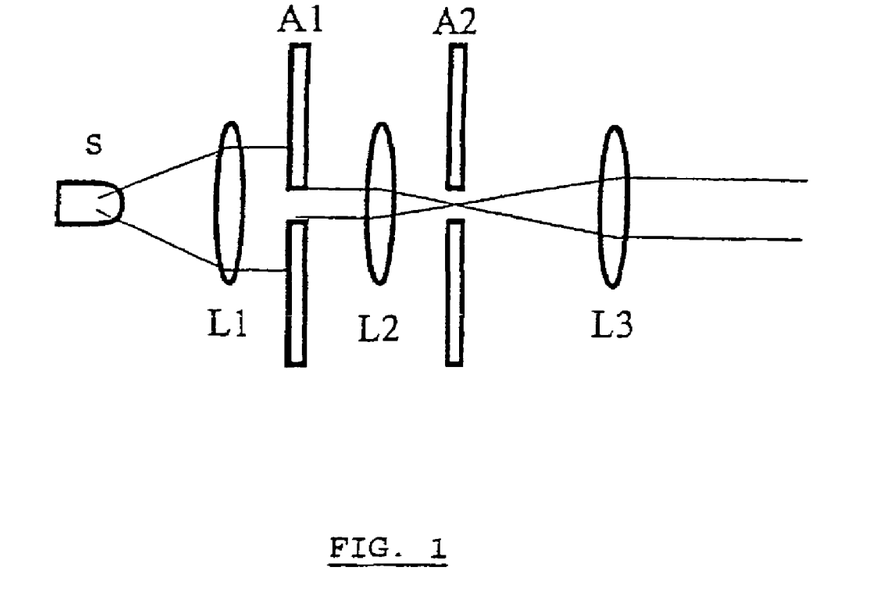
FIG. 1 shows a first embodiment of a spatially partially coherent source, produced from a spatially incoherent source.

A first type of light source that can be used in the instrument corresponds to a partially spatially coherent source as shown in FIG. 1. An achromatic lens L1 collimates the light rays emitted by an extended spatially incoherent wavelength-filtered source S, for example an LED (light-emitting diode), to a first iris diaphragm A1 of adjustable aperture. The aperture A1 limits the angular spectrum of the source so as to increase the spatial coherence of the light. A second achromatic lens L2 creates a secondary source in its focal plane in which a second iris diaphragm A2 limits the size of the source. A third lens L3 forms a collimated beam. For digital holography, the focal lengths of L1, L2, L3 are, for example, 100 mm.

Figure 2:
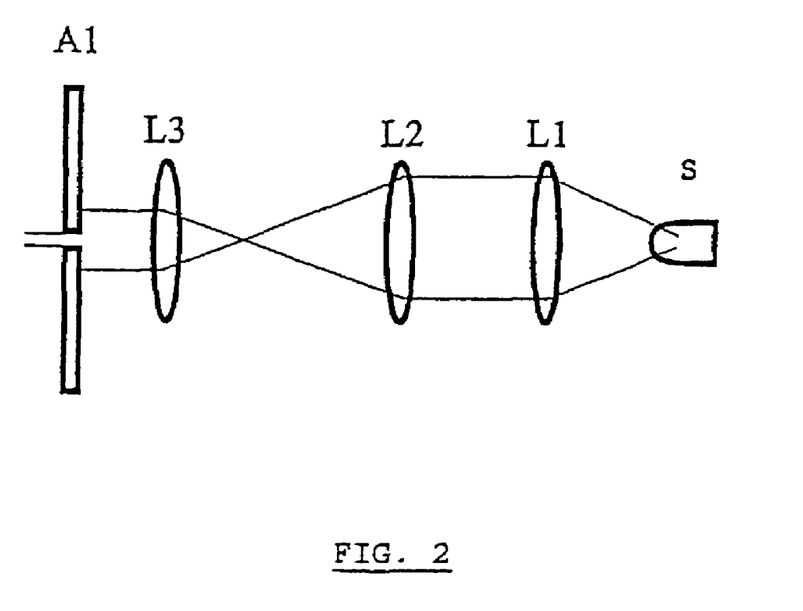
FIG. 2 shows a second embodiment of a spatially partially coherent source, produced from a spatially incoherent source.

A second type of light source that can be used in the instrument corresponds to a partially coherent source as shown in FIG. 2. A lens L1 collimates the light rays emitted by an extended spatially incoherent wavelength-filtered source S, for example an LED (light-emitting diode). To obtain a homogeneous light field, the light rays from this source may be conveyed, from the LED to the lens L1, via an optical fiber whose core is liquid. The set of lenses L2 and L3 forms a collimated beam. The spatial filter A1 limits the angular spectrum of the source so as to increase the spatial coherence of the light.

Figure 3:
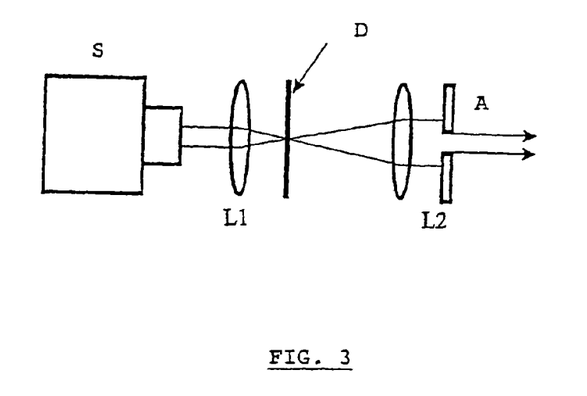
FIG. 3 shows a third embodiment of a spatially partially coherent source, produced from a spatially coherent source.

It is also possible to use in the instrument a laser source S made partially incoherent. FIG. 3 shows the operating principle of such a source conventionally used in optics. A parallel-ray laser beam is focused by a lens L1. A rotating diffuser D is placed behind the focal point so as to form a light spot whose diameter is sufficient to illuminate the field of view of the microscope. The diffuser creates a speckle field that varies with the rotation of the diffuser. A lens L2 is placed so that its focal point lies in the plane of the rotating diffuser.

An aperture A is then placed behind the lens so as to be able to increase the size of the speckle grains. By using a motor rotating sufficiently rapidly compared with the exposure time of the image recording system, it may be shown that such a source is equivalent to a spatially partially coherent source as described above. The width of the spatial coherence is directly related to the size of the speckle grains, which is adjusted by the diameter of the aperture.

Figure 4:
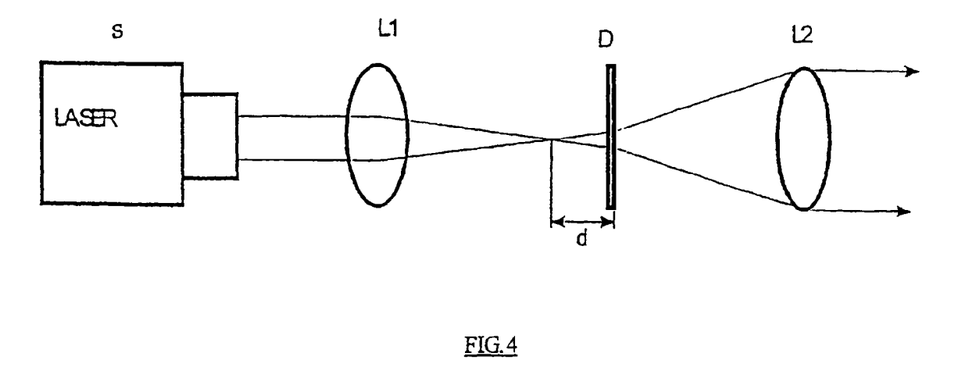
FIG. 4 shows a fourth embodiment of a spatially partially coherent source, produced from a spatially coherent source.

Another type of collimated and partially coherent source based on a coherent source, that can be used in the instrument, is shown in FIG. 4. A laser beam emitted by a laser source S is focused near a ground glass plate (D) by a lens (L1). The ground glass plate scatters the light. A lens (L2) placed behind the ground glass plate collimates the light scattered by said plate. By adjusting the distance (d) between the focal point and the ground glass plate, the size of the collimated-beam speckle grains is adjusted.

Microscope Operating in Digital Holography

Figure 5:
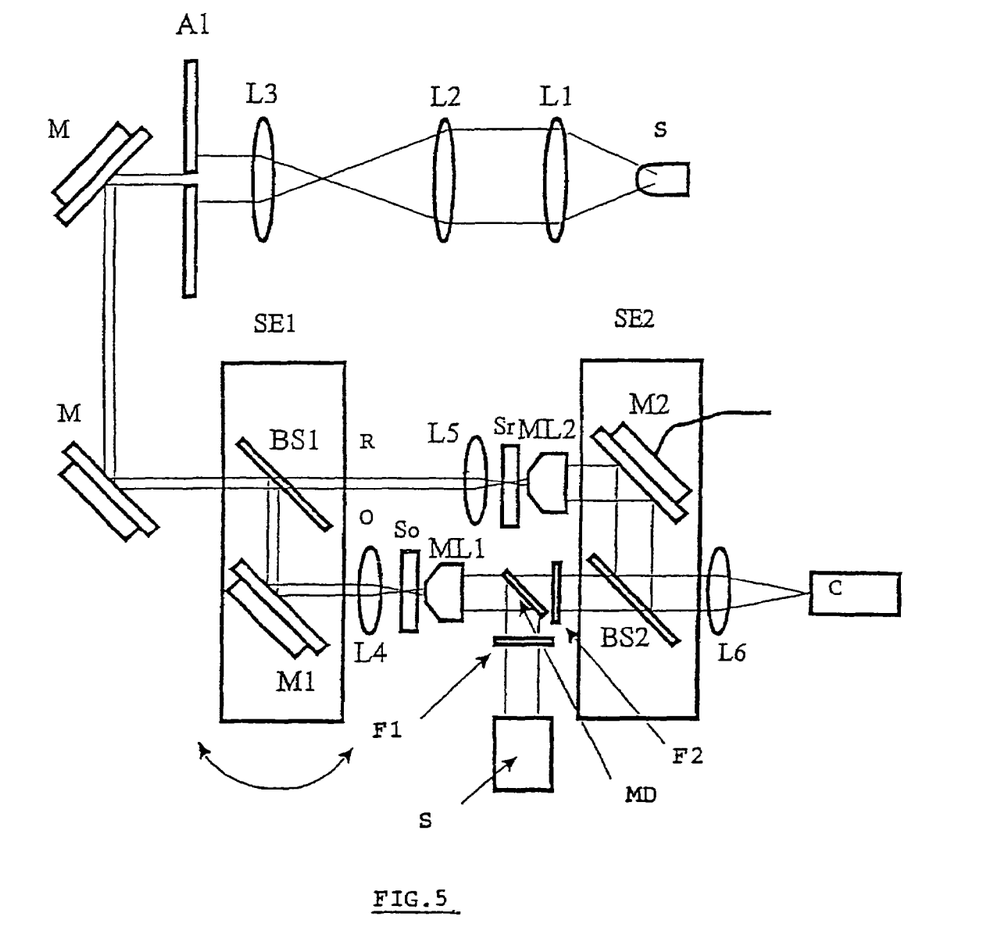
FIG. 5 shows a preferred embodiment of an instrument, comprising one preferred embodiment of a microscope which uses a spatially partially coherent source as described in FIG. 2.

FIG. 5 shows the plane of one embodiment of a microscope used in the instrument. The interferometer of the microscope operating in digital holography is of the Mach-Zehnder type and comprises two subassemblies SE1 and SE2. Each of these has a beam splitter, BS1 and BS2 respectively, and a mirror, M1 and M2 respectively. The source for the digital holography is a partially spatially coherent source such as one of those described above. Said source illuminates the beam splitter BS1. One portion of the beam is transmitted by BS1 and one portion is reflected toward the mirror M1.

The first subassembly SE1 is used to form two parallel light beams—the object beam O and the reference beam R. This first subassembly SE1 is mounted on a rotary table, while the second subassembly SE2 is fixed or movable (movable in rotation). This makes it possible to adjust the equalization (i.e., to equalize) of the optical path of the two beams—the object beam O and the reference beam R—of the interferometer. As explained hereafter, the first subassembly SE1, and the second subassembly when movable, thus function as equalization means for equalizing the optical path lengths between the reference beam R and the object beam O.

As regards the object beam, a lens L4 (focusing means placed in the interferometer) focuses the light beam onto the object or specimen contained in its observation cell So. The object is observed with a microscope objective ML1 advantageously suitable for observing in fluorescence (the various possible magnifications in conventional microscopy can be used). The pair of lenses L4-ML1 forms an a focal system. The objective ML1, in combination with the lens L6 which functions as focusing means and is placed between the interferometer and the recording means, produces the image of a plane passing through the specimen on the sensitive plane of said recording means (CCD camera C). However, it is obvious for the man skilled in the art that the microscope objective ML1 is not necessarily adapted for fluorescence measurements when the microscope is used alone (not coupled to a fluorescence excitation source) for just obtaining three-dimensional images of a specimen.

Similarly, as regards the reference beam R, the lens L5 (focusing means placed in the interferometer) focuses the light beam either onto an observation cell Sr, identical to that having the specimen (So) but without the latter being present, or onto a transparent material of suitable composition and thickness, such as for example glass. This arrangement makes it possible to optimize the equalization of the optical path of the two beams (object and reference beams) of the interferometer.

It means that the reference cell or the material of suitable composition and thickness Sr functions as a compensation means for optimizing the equalization of the optical path lengths between the object beam O and the reference beam R, equalization which is obtained by the movement of the first subassembly SE1 and/or the second subassembly SE2.

A microscope objective ML2, identical to ML1, is placed in the reference beam. The pair of lenses L5-ML2 also constitutes an a focal system.

Similarly, the objective ML2, in combination with the lens L6, produces the image of a plane passing through the element Sr (reference cell or suitable equivalent material) on the sensitve plane of the recording means (CCD camera C).

The optical paths ML1-L6 and ML2-L6 are adjusted to be identical.

The second subsystem SE2, which comprises the mirror M2 and the beam splitter BS2, is used to combine the object beam O with the reference beam R. The combined object O and reference R beams interfere in the sensitive plane of the camera (recording means) (labeled C in FIG. 5).

An important technical characteristic of the microscope of the invention is related to the presence of the focusing means L6 placed after the interferometer and in front of the recording means C(CCD camera C) in such a way that the back focal plane of said focusing means L6 is in the sensitive plane of the recording means so as to obtain, in operating conditions, an invariant positioning of the object beam O and the reference beam R on the sensitive plane of the recording means when the first subassembly SE1 and/or the second subassembly SE2 are moved.

As indicated below, the implementation of digital holography requires knowledge of the optical amplitude measured in a plane of sharpness that intercepts the specimen. The optical amplitude may be determined from the interference patterns by two methods:

(i) "the carrier or Fourier transform method", when both the first subassembly SE1 and the second subassembly SE2 are movable (movable in rotation). Using this method, subassemblies are moved and the object and reference beams are incident on the CCD camera at a small angle so as to obtain, when no specimen is being analyzed, a linear array of interference fringes. The optical phase change introduced by the specimen is then manifested by a variation in the shape of the fringes. The amplitude is determined by Fourier transform analysis;

(ii) the "phase-stepping method", when the second subassembly SE2 is fixed and the mirror M2 of the subassembly SE2 is movable in translation; the mirror M2 is provided with a system for piezoelectric displacement along its optical axis, which allows the reference optical path to be changed by precise fractions of a wavelength. This method consists in recording several images phase-shifted by a constant fraction of the wavelength. The combination of these interferograms makes it possible, by computer processing, to calculate the light amplitude emerging from the specimen.

The microscope can operate in direct or inverse microscopy mode depending on the requirements.

Figure 6:
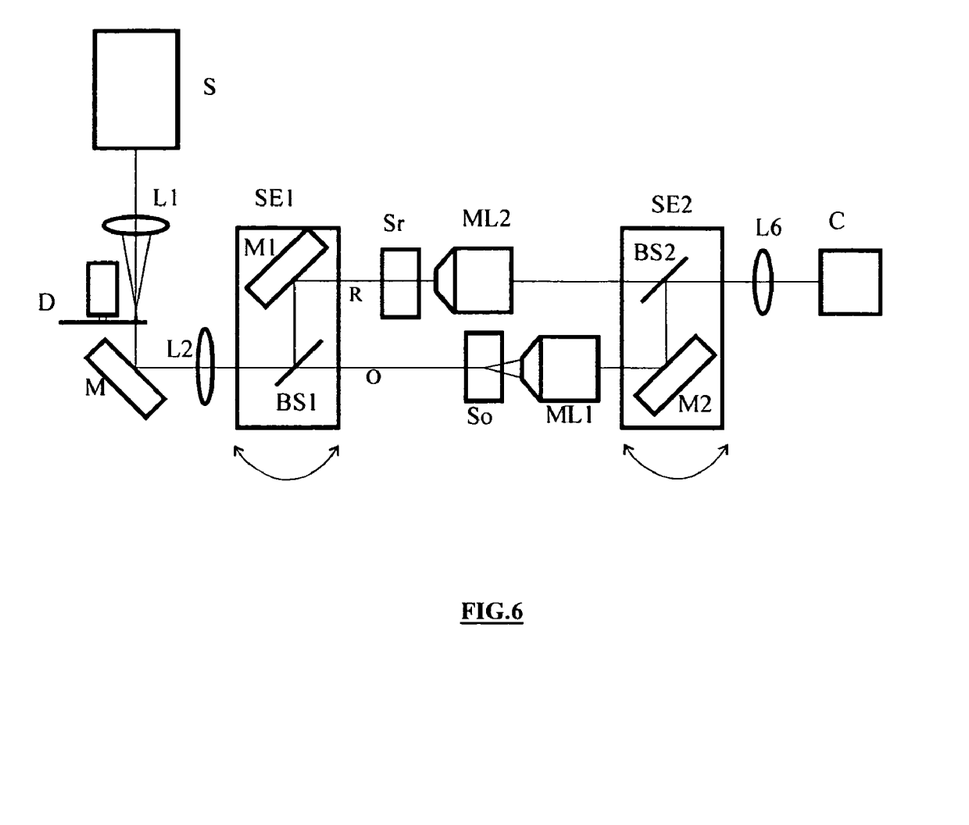
FIG. 6 shows another preferred embodiment of a microscope, using a partially spatially coherent light source as described in FIG. 4.

An alternative embodiment of a microscope comparatively to the one presented on FIG. 5 is illustrated by FIG. 6.

This alternative embodiment differs from the embodiment disclosed in FIG. 5 in that the second subassembly SE2 is necessarily movable in rotation. The second subassembly SE2 can be used as equalization means for equalizing the optical path lengths of the object beam and the reference beam.

The analysis of the interference patterns could be carried out using the Fourier transform method, and for this reason it is not necessary to move in translation the mirror M2.

As compared to the microscope disclosed in FIG. 5, this microscope similarly comprises focusing means L6 which are placed after the interferometer and in front of the recording means C(CCD camera C) in such a way that the back focal plane of said focusing means L6 is in the sensitive plane of the recording means so as to obtain, in operating conditions, an invariant positioning of the object beam O and the reference beam R on the sensitive plane of the recording means when the second subassembly SE2 is moved.

Similarly to the microscope of FIG. 5, this microscope also comprises compensation means for optical path compensation between the object beam O and the reference beam R, said means being located in the optical path of the reference beam R between the first subassembly SE1 and the second subassembly SE2.

This compensation means can be a reference cell Sr as illustrated on FIG. 6, which is similar to the object cell So except that this reference cell does not include a sample.

The compensation means can also correspond to a transparent material of suitable composition and thickness.

However, in this embodiment, there are no equivalents for first focusing means and second focusing means L4 and L5.

Moreover, the partially spatially coherent light source is of another type (type of source as represented on FIG. 4, see description of possible types of sources above as reference).

Figure 7:
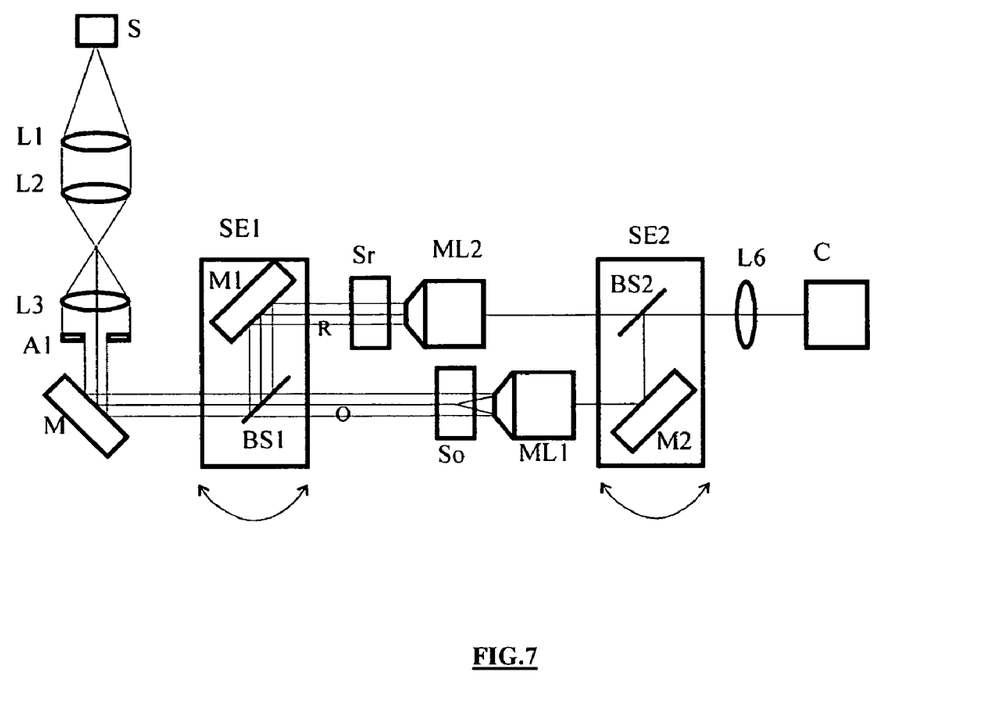
FIG. 7 shows another preferred embodiment of a microscope, using a partially spatially coherent light source as described in FIG. 2.

FIG. 7 presents an other alternative embodiment of the microscope which essentially differs from the microscope illustrated by FIG. 6 by the type of source used as partially spatially coherent light source (type of source as represented on FIG. 2, see description of possible types of sources above as reference).

Instrument for Fluorescence

Reference is made to FIG. 5 for illustrative purposes. The FIG. 5 presents one preferred embodiment of an instrument, wherein a microscope as describe hereabove is coupled to a fluorescence excitation light source S'. As shown, in FIG. 5, the fluorescence excitation source S' is placed in reflection mode. As indicated above, it is possible to place this source so as to operate in transmission mode.

Fluorescence in Reflected Light

In this configuration, which corresponds to that shown in FIG. 5, the source S' is either a mercury vapor lamp or a quartz-halogen lamp, or else a source that emits light within a range of short wavelengths that is needed for fluorescence excitation. Where appropriate, this source may be a laser. The light rays, collimated by a lens, enter an excitation filter F1 selected according to the fluorochrome used and are reflected by a suitable dichroic mirror MD onto the specimen through the objective.

The fluorescent light emitted by the fluorochromes contained in the specimen passes through the dichroic mirror MD, which is transparent at these longer wavelengths, passes through a stop filter F2, placed so as to block any short wavelengths, and is recorded by the camera.

Materials of suitable composition and thickness, for example glass, may be added in the reference beam in order to optimize the equalization of the optical path of the two interferometer beams.

Fluorescence in Transmitted Light

For this configuration, there are two possible constructions:

(i) a single-source construction: the single source used is that provided for the microscope operating in digital holography, but it is used simultaneously as a fluorescence excitation source as it emits in a range of short wavelengths. This makes it possible both to create the hologram of the object and to excite the fluorochromes of the specimen;

(ii) a two-source construction: the source specifically for the microscope operating in digital holography is combined with the source that emits the light needed for exciting the fluorochromes in the two following ways: either the source needed for the fluorescence is placed just in front of the beam splitter BS1 or this source is placed just in front of the lens L4 that focuses the light rays onto the specimen.

Coupling of the Digital Holography and Fluorescence Signals for the 3D Reconstruction of the Fluorescence Signals As described above, the instrument comprises two coupled optical subsystems for:

(i) recording the interferometric images in transmission of the specimen;

(ii) recording the fluorescence image of the specimen activated by the fluorescence excitation source.

These images are formed by the a focal system consisting of the pair of lenses ML1-L6 that produces the sharp image of a plane perpendicular to the optical axis of the specimen on the sensitive surface of the camera C (sensitive plane of the recording means C). The interferometric and fluorescence images are recorded sequentially:

(i) the fluorescence source is masked by a shutter and the interferometric image or images are recorded;

(ii) the source for the interferometric recording is masked or turned off and the fluorescence image or images are recorded.

When the thickness of the specimen is smaller than the depth of field of the imaging device, the image of the specimen is sharp everywhere. However, and it is this case to which the present development relates, when the thickness of the specimen exceeds the depth of field, those parts of the specimen beyond the depth of field region give fuzzy parts in the image.

Since the specimen is observed by a camera C using an a focal lens system ML1-L6, the interferometric and fluorescence signals are perfectly superposed at the sensor and the planes of sharpness are common for both types of illumination thanks to the use of achromatic optical components ML1-L6.

Role of the Interferometric or Holographic Recording

The interferometric recording allows precise measurement of the complex optical amplitude in the sharp plane of the specimen. The coherent or partially coherent interferometric source (comprising the source S) is activated and illuminates, as a collimated beam, the beam splitter BS1.

One portion of this beam, called the object beam, follows the path BS1-M1-L4-So-ML1-BS2-L6-C. The phase and the amplitude of this beam are modulated by the specimen contained in the object cell So.

The other portion of the beam, called the reference beam, follows the path BS1-L5-Sr-ML2-M2-BS2-L6-C. The phase and the amplitude of this beam are modulated by the reference cell Sr.

The object and reference beams interfere on the sensitive surface (sensitive plane) of the camera C. The shape of the interference pattern is influenced by the relative optical phase changes introduced by the specimen So and the reference cell or equivalent material Sr. Since the reference cell Sr is an experimental cell similar to the object cell So, but without the specimen under investigation, or an equivalent suitable material, the shape of the interference pattern is significantly influenced only by the optical phase changes introduced by the specimen under investigation.

The first objective is to measure the emergent complex optical amplitude from the specimen on the basis of the interference pattern or patterns measured by the camera. To do this, two methods conventional in interferometry are available:

(i) the Fourier transform method [1];

(ii) the phase shift method.

Knowing the complex optical amplitude in the plane of sharpness of the specimen, digital holography methods are used to calculate the complex amplitudes in parallel planes [2-6]. These methods consist in calculating, by numerical methods, the optical field using the Fourier optics propagation laws (Kirchhoff-Fresnel equation). It is thus possible to calculate the complex light amplitudes in planes that are away from the initial depth of field region of the imaging system. Thus, those image regions that were recorded fuzzy are made sharp by using these methods.

A complex optical amplitude $u(x,y)$ in an $(x,y)$ plane is given by:

$$u(x,y)=\sqrt{I(x,y)}\exp\{i\alpha(x,y)\} \qquad (1)$$

where:

$I(x,y)$ is the light intensity at the point $(x,y)$;

$\alpha(x,y)$ is the optical phase at the point $(x,y)$; and $i$ is the imaginary number such that $i^2=-1$.

The interferometric method therefore amounts to determining, in the plane in which the image is produced, the quantities $I(x,y)$ and $\alpha(x,y)$ so as to be able to calculate, by digital holography, the optical amplitude $u_d'(x',y')$ in the parallel planes separated by distances d. This operation is formally written as:

$$u_d'(x',y')=R[d]u(x,y) \qquad (2)$$

where: $R[d]$ is the Kirchhoff-Fresnel operator.

Several numerical evaluations of this expression exist in the literature [2].

Recording of the Fluorescence Signal

When the fluorescence excitation source is activated, the fluorescent substances distributed within the specimen emit light isotropically, giving rise to a signal detected by the CCD video camera. If we consider the emission by a point (x0,y0) of the specimen located at a distance d from the plane, the image of which is formed by the lens pair ML1-L6, owing to the fact that the objective of the microscope has a finite aperture, the fluorescence-emitting point produces, in the plane of the object whose image is formed, a light disk that can be observed by the video camera.

This distribution of the light intensity is denoted by, $I_p$(x-x0, y-y0) where the subscript p indicates that it is the fluorescence signal that is considered.

The diameter D of the luminous disk is given, to a first approximation, by:

$$D = \frac{d}{fnumber_{ML1}} \quad (3)$$

where $fnumber_{ML1}$ is the ratio of the focal length of ML1 to the diameter of its aperture.

It should be noted that equation (3) must be corrected for the very short distances d with which the diffraction effects in incoherent illumination have to be considered. However, for these distances d, the image of the point source lies in the depth of field region and therefore requires no subsequent manipulation as regards sharpness.

In the case of more complex specimens, having several emission regions that may be located at different distances d from the plane of sharpness, a light intensity distribution is obtained that is expressed as the sum of elementary contributions: $I_p$(x-x0,y-y0).

Coupling Between the Complex Amplitude of the Digital Holography Signal and the Fluorescence Signal The concept forming the subject-matter of the present patent application is the coupling between the digital holography signal and the fluorescence signal so as to be able to manipulate the fluorescence signal and be able to sharpen, by a digital holography numerical process, fluorescence signals that have been recorded fuzzy.

To be able to accomplish this coupling, it is necessary for the regions within the biological specimen that exhibit fluorescence to have optical properties (optical absorbence and/or refractive index) that are different from the nonfluorescent regions that surround them. It should be pointed out that this condition is satisfied in many applications in cell biology, since fluorescence is used for labeling cell organelles that are also visible by optical microscopy in phase contrast. This demonstration by phase contrast reveals a local variation in refractive index and/or of absorbence of the organelles.

If one considers a limited region of fluorescence within the biological specimen that is also a region in which there is a local index and/or absorbence change relative to a constant background and if it is assumed that this region lies at a distance d from the plane of sharpness of the specimen, the fluorescence region, as described above, gives rise to a light spot of intensity $I_p$(x-x0,y-y0). The light amplitude measured by interferometry is given by equation (1):

$$u(x,y) = \sqrt{I(x,y)} \exp\{i\alpha(x,y)\}.$$

Firstly, an equivalent fluorescence amplitude is constructed by:

$$u_p(x,y) = A\sqrt{I_p(x-x0,y-y0)}\sqrt{I(x,y)}\exp\{i\alpha(x,y)\} \quad (4)$$

where A is a multiplicative constant that does not play a key role in the present discussion.

Equation (4) weights the interferometric amplitude by the intensity of fluorescence so as to amplify the fluorescence-influenced region.

Next, digital holography reconstruction is applied in order to reconstruct the sharp image of the fluorescence:

$$u_p'(x',y') = R[-d]u_p(x,y) \quad (5)$$

Next, the light intensity $u_p'^*(x',y')u_p'(x',y')$ is then calculated in order to obtain the sharp image of intensity of the fluorescence spot.

In practice, the interferometric light amplitude and the fluorescent light spot are measured without knowing the distance d. The digital holography reconstruction technique is then applied incrementally in order to achieve the sharpest image of the fluorescence spot.

If one now considers the case in which, within the specimen, there are several limited regions with refractive index and/or absorbence variations, among which only some of these regions exhibit fluorescence emission, two cases may arise:

(i) 1st case: the interferometry and fluorescence signals are separate in the sharp plane of the specimen. In this case, the method as described above may be used directly;

(ii) 2nd case: the interferometry and fluorescence signals overlap, at least partially, in the sharp plane of the specimen.

In this second case, the use of the method as described above may give rise to false reconstructions of the fluorescent regions, which are in fact not so. This is because, if we consider, on the one hand, the interferometry signals due to two regions of index and/or absorbence variations that are superposed and, on the other hand, that only one of these two regions exhibits fluorescence, since the fluorescence spot at least partially overlaps the interferometric signals emanating from the two regions, the use of the above method will give a significant contribution to the fluorescence for the two regions. In this case, many correction methods may be implemented so as to reconstruct only the relevant region. Mention may be made, by way of example, of an iterative correction procedure. The initial fluorescence distribution in the plane of sharpness will be called D0. At the first iteration, the above holographic reconstruction method is used, which gives fluorescence contributions for both regions. The result of this reconstruction will be called the configuration C1. Next, using the propagation laws of incoherent optics, the fluorescent light distribution, called D1, in the plane of sharpness of the specimen, which corresponds to C1, is calculated. D1 and D0 are compared so as to apply a correction to C1 and obtain a second configuration C2. From this, a new fluorescence distribution D2 is calculated by the laws of incoherent optics and the iterative correction process is thus repeated until a sufficiently small difference is obtained between the fluorescence distribution DN (Nth iteration) calculated by the laws of incoherent optics and the fluorescence distribution D0. Many numerical optimization methods may be used to implement such an optimization procedure. By way of example, mention may be made of the simulated annealing methods based on random searching for the minimization of a cost function, which in the present case could be $(DN-D0)^2$ [7].

To summarize, combining a fluorescence instrument with a microscope operating in digital holography in order to measure, in three dimensions, fluorescent regions of microspecimens, offers many advantages over the currently known techniques.

A first advantage is that certain embodiments, compared with conventional fluorescence microscopy, allows a three-dimensional image of the fluorescence to be obtained without it being necessary to move the specimen along the optical axis of the system.

Furthermore, the phase and amplitude information provided by the digital holography may be used to remove, at each point, the parasitic fluorescence by digital processing.

Compared with confocal microscopy, certain embodiments also have particular advantages.

One of these advantages is that certain embodiments are much less complex to implement than confocal microscopy.

Another advantage, in certain embodiments, is that it makes it possible to use an extended range of light sources to generate the fluorescence signal, and it therefore extends the wavelength range available to cover the applications. This also allows the use of sources that are less aggressive to biological specimens.

It should also be noted that, compared with confocal microscopy, certain embodiments allow information to be recorded about the entire specimen simultaneously over the volume and with a very small time delay between each acquisition (typically 1/25 s) for recording the fluorescence, in such a way that the temporal distortion introduced by the scanning in confocal microscopy is eliminated.

In conclusion, the method described herein, which consists in coupling interferometry signals with fluorescence signals, makes it possible to locate, in three dimensions, and with sharp images, the regions that exhibit fluorescence within a specimen. This method is advantageously applicable in the field of embryology in which biologists wish to examine the change in and dynamics of living embryos which very rapidly exhibit thicknesses that exceed the depth of field of optical microscopes. Thus, certain embodiments may allow, for example, a posteriori three-dimensional analysis of the movement of cells labeled by fluorochromes.

Furthermore, the holographic microscope also has a number of advantages over the instruments of the prior art, in particular compared with the holographic microscope described in the article "Improved three-dimensional imaging with digital holography microscope using a partial spatial coherent source" by F. Dubois et al., *Appl. Opt.* 38, pp. 7085-7094 (1999).

Indeed, a different characteristic of the microscope described herein as compared to the microscope described in the article "Improved three-dimensional imaging with digital holography microscope using a partial spatial coherent source" by F. Dubois et al., *Appl. Opt.* 38, pp. 7085-7094 (1999) lies in the presence of the focusing means L6, which are not present in the prior art document and which are placed after the interferometer and in front of the recording means in a specific manner.

More precisely, as already mentioned hereabove, the focusing means L6 in the microscope of the invention is placed in such a way that the back focal plane of said focusing means L6 is in the sensitive plane of the recording means so as to obtain, in operating conditions, an invariant positioning of the object beam O and the reference beam R on the sensitive plane of the recording means when the second subassembly SE2 is moved.

This technical characteristic of the present microscope contributes to the obtention of three-dimensional images of a specimen of higher quality.

Moreover, comparatively to the holographic microscope described in that publication, in the particular embodiment of the microscope illustrated on FIG. 5, the lens L4 and the lens L5 which are used to focus the light in the object cell and reference cell respectively (or other optical path compensation means) are located within the interferometer itself, specifically in front of the objectives, ML1 and ML2 respectively, and no longer outside the interferometer. Consequently, from that point of view also, the light rays that reach the beam splitter BS1 are collimated using mirrors M (FIG. 5) and the position of the focal point is not modified when the position of the incident ray relative to the optical axis varies. This feature allows much more effective use of the rotary table and makes equalization of the optical paths of the reference and object beams easier. This adjustment possibility is preferable in a holographic microscope having a partially coherent light source.

Furthermore, this technical characteristic of the present microscope also contributes to the obtention of three-dimensional images of a specimen of higher quality.

In addition, in the holographic microscope, the presence either of the reference observation cell Sr, similar to the cell So that contains the specimen, or of a transparent material of suitable composition and thickness may also be used to improve the equalization of the object 0 and reference R optical paths.

This technical characteristic of the present microscope also contributes to the obtention of three-dimensional images of a specimen of higher quality.

Finally, compared with that publication, the microscope offers the possibility of using three other types of partially coherent sources that have proved to be superior to that used in the publication.

LITERATURE REFERENCES

1. M. Takeda, H. Ina and S. Kobayashi, "Fourier transform method of fringe pattern analysis for computer based topography and interferometry", J. Opt. Soc. Am. 72, 156-160 (1972).
2. F. Dubois, L. Joannes and J.-C. Legros, "Improved three-dimensional imaging with digital holography microscope using a partial spatial coherent source", Appl. Opt. 38, 7085-7094 (1999).
3. E. Cuche, F. Bevilacqua and C. Depeursinge, "Digital holography for quantitative phase contrast imaging", Opt. Let. 24, 291-293 (1999).
4. T. Zhang and I. Yamaguchi, "Three-dimensional microscopy with phase-shifting digital holography", Opt. Let. 23, 1221-1223 (1998).
5. Skarman, Wozniac and Becker, "Simultaneous 3D-PIV and temperature measurement using a New CCD based holographic interferometer", Flow Meas. Instr. 7, No. 1, pp. 1-6 (1996).
6. Y. Takaki and H. Ohzu, "Hybrid holographic microscopy: Visualization of three-dimensional object information by use of viewing angles", Appl. Opt. 39, 5302-5308 (2000).
7. S. Kirkpatrick, C. D. Gelatt, Jr. and M. P. Vecchi, "Optimization by Simulated Annealing", *Sciences* 220, 671-679 (1983).
8. B. W. Schilling, T.-C. Poon, G. Indebetouw, B. Storrie, K. Shinoda, Y. Suzuki and M. H. Wu, "Three-dimensional holographic fluorescence microscopy", Optics Letters 22, No. 19, 1506-1508 (1997).

The invention claimed is:

1. A digital holographic microscope for obtaining without scanning three-dimensional images of a specimen to be studied, comprising a light source, an interferometer, a recorder defined by a sensitive plane and a processor, said microscope being conceived in such a manner that in operating conditions said light source provides a partially spatially coherent light beam, said interferometer separates said partially spatially coherent light beam into a reference light beam and an object light beam, said object beam illuminates a specimen preliminary placed therein, said object and reference beams are recombined to produce interference patterns in the sensitive plane of said recorder, the recorder records said interference patterns and said processor processes said recorded interference patterns and reconstructs three-dimensional images of the specimen, wherein the interferometer comprises:
- a movable first subassembly that comprises a beam splitter and a mirror, able to form two parallel beams-an object beam and a reference beam, from the source light beam;
- a movable second subassembly comprising a beam splitter and a mirror so as to combine said object beam and said reference beam into a recombined light beam;
- an object cell, to receive the specimen to be studied, said object cell being placed in the optical path of the object beam between the first subassembly and the second subassembly;
- a first microscope objective located in the optical path of the object beam between the first subassembly and the second subassembly, downstream of the object cell;
- a compensator to optimize the equalization of the optical path lengths between the object beam and the reference beam, said compensator being located in the optical path of the reference beam between the first subassembly and the second subassembly;
- a second microscope objective located in the optical path of the reference beam between the first subassembly and the second subassembly, downstream said compensator;

wherein the microscope further comprises a focuser defined by a back focal plane, said focuser being placed between the interferometer and the recorder in such a way that the back focal plane of said focuser is in the sensitive plane of the recorder and that an invariant positioning of the recombined light beam on the sensitive plane of the recorder is maintained when the second subassembly is moved in operation.

2. The microscope according to claim 1, wherein the first subassembly and the second subassembly are movable in rotation.

3. The microscope according to claim 2, wherein the movements in rotation of the second subassembly allow in operating conditions the implementation of a Fourier transform method by the processor in order to process the interference patterns.

4. The microscope according to claim 1, wherein the interferometer further comprises a first focuser focusing the object beam onto the object cell, and a second focuser focusing the reference beam onto said compensator.

5. The microscope according to claim 4, wherein the movements in translation of the mirror of the second subassembly allow in operating conditions the implementation of a phase-stepping method by the processor in order to process the interference patterns.

6. The method according to claim 5, wherein the mirror of the second subassembly is mounted on a piezo-electric motor.

7. The microscope according to claim 6, further comprising a director device to direct the source light beam onto the first subassembly at the beam splitter.

8. The microscope according to claim 7, wherein the director device comprises mirrors.

9. The microscope according to claim 1, wherein the partially spatially coherent light source comprises the following elements: a source emitting light of small spectral width, a first lens, a first aperture, a second lens, a second aperture and a third lens, the relative arrangement of these various elements being such that, when the source is operating, the light emitted by the light-emitting source encounters, in succession, the first lens, the first aperture, the second lens, the second aperture and the third lens, and the light at the exit of the third lens is collimated light.

10. The microscope according to claim 1, wherein the partially spatially coherent light source comprises: a source emitting light of small spectral width, an optical fiber, a first lens, a second lens, a third lens and an adjustable aperture, the relative arrangement of these various elements being such that, when the source is operating, the light emitted by the light-emitting source passes firstly through the optical fiber so as to have a homogeneous light field and then encounters the first lens, then the second lens and the third lens in order to obtain collimated light at the aperture.

11. The microscope according to claim 1, wherein the partially spatially coherent light source of said microscope comprises: a laser source, a first lens, a rotating diffuser, a second lens and an aperture, the relative arrangement of these various elements being such that, when the source is operating, the laser beam emitted by the laser source firstly passes through the first lens, then the rotating diffuser, which is placed behind the focal point of said first lens, then the second lens, placed at its focal length with respect to the plane of the rotating diffuser, and then said aperture.

12. The microscope according to claim 1, wherein the partially spatially coherent light source comprises: a laser source, a first lens, a rotating diffuser, and a second lens, the relative arrangement of these various elements being such that, when the source is operating, the laser beam emitted by the laser source firstly passes through the first lens, then the diffuser and then the second lens, the laser beam at the exit of the first lens being focused at a focal point located upstream of the diffuser at an adjustable distance from the diffuser.

13. The microscope according to claim 12, wherein the rotating diffuser comprises a ground glass plate.

14. The microscope according to claim 1, wherein said compensator comprises a reference cell similar to the object cell but not including the specimen to be studied, or a transparent material of suitable thickness and suitable composition.

15. The microscope according to claim 1, wherein the first subassembly and the second subassembly are movable in rotation.

16. The microscope according to claim 15, wherein the movements in rotation of the second subassembly allow in operating conditions the implementation of a Fourier transform method by the processor in order to process the interference patterns.

* * * * *

UNITED STATES PATENT AND TRADEMARK OFFICE
CERTIFICATE OF CORRECTION

| | |
|---|---|
| PATENT NO. | : 7,463,366 B2 |
| APPLICATION NO. | : 11/284768 |
| DATED | : December 9, 2008 |
| INVENTOR(S) | : Franck Dubois et al. |

It is certified that error appears in the above-identified patent and that said Letters Patent is hereby corrected as shown below:

Title Page; item (30):

Page 1, Column 1, after "Continuation-in-part of application No. 10/742,054...filed on Jul. 1, 2002.", insert a centered section header entitled -- Foreign Application Priority Data --.

Page 1, Column 1, on the next line after the preceding correction, insert -- Jun. 29, 2001 (EP)........EP 01870147.4 --.

Page 1, Column 1, on the next line after the preceding correction, insert -- Dec. 18, 2001 (EP)........EP 01870281.1 --.

Column 9, Line 10, change "a focal" to -- afocal --.

Column 9, Line 38, change "a focal" to -- afocal --.

Column 9, Line 42, change "sensitve" to -- sensitive --.

Column 11, Line 50, change "a focal" to -- afocal --.

Column 12, Line 1-2, change "a focal" to -- afocal --.

Signed and Sealed this

Thirtieth Day of March, 2010

David J. Kappos
*Director of the United States Patent and Trademark Office*